United States Patent [19]

Morozowich

[11] 4,011,249

[45] * Mar. 8, 1977

[54] SUBSTITUTED KETO AND ALKOXY CARBONYL ESTERS OF 16-SUBSTITUTED $PGE_2$ TYPE COMPOUNDS

[75] Inventor: Walter Morozowich, Kalamazoo, Mich.

[73] Assignee: The Upjohn Company, Kalamazoo, Mich.

[ * ] Notice: The portion of the term of this patent subsequent to July 8, 1992, has been disclaimed.

[22] Filed: Nov. 21, 1975

[21] Appl. No.: 634,124

Related U.S. Application Data

[62] Division of Ser. No. 523,568, Nov. 14, 1974.

[52] U.S. Cl. .......................... 260/390; 260/468 D; 260/471 R; 260/473 R; 260/476 R
[51] Int. Cl.² ...................................... C07C 177/00
[58] Field of Search .......... 260/468, 476, 471, 473, 260/390

[56] References Cited

UNITED STATES PATENTS 3,839,062   7/1975   Morozowich ..................... 260/395

Primary Examiner—Robert Gerstl
Attorney, Agent, or Firm—Morris L. Nielsen; Bruce Stein

[57] ABSTRACT

Substituted phenyl and naphthyl esters of $PGE_2$ analogs, including the 16-alkyl, 16-fluoro, 16-phenoxy, and phenyl-substituted analogs, and their 15-epimers, and their racemic forms, and processes for producing them are disclosed. The products are useful for the same pharmacological and medical purposes as these $PGE_2$ analogs, and are also useful as a means for obtaining highly purified 16,16-dimethyl-$PGE_2$, 16-phenoxy-17,18,19,20-tetranor-$PGE_2$, and 17-phenyl-18,19,20-trinor-$PGE_2$.

11 Claims, No Drawings

SUBSTITUTED KETO AND ALKOXY CARBONYL ESTERS OF 16-SUBSTITUTED PGE₂ TYPE COMPOUNDS

This is a division of application Ser. No. 523,568, filed Nov. 14, 1974.

BACKGROUND OF THE INVENTION

This invention relates to novel ester derivatives of prostaglandin E₂ analogs (hereinafter identified as "PGE₂" analogs), including the 16-alkyl, 16-fluoro, 16-phenoxy, and phenyl-substituted analogs, and their 15-epimers, and their racemic forms and to processes for producing them.

PGE₂ is represented by the formula,

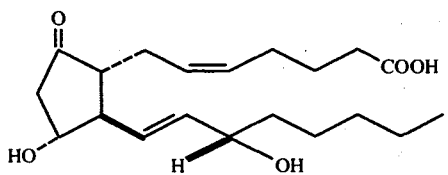

A systematic name for PGE₃ is 7-{3α-hydroxy-2β-[(3s)-3-hydroxy-trans-1-octenyl]-5-oxo-isocyclopentyl) -cis-5-heptenoic acid. PGE₂ is known to be useful for a variety of pharmacological and radical purposes, for example labor induction and abortion in pregnant animals, including humans, menstrual regulation in both pregnant and non-pregnant animals, including humans, reduction and control of gastric secretion, and as a hypotensive agent to reduce blood pressure in mammals, including humans. See Bergstrom et al., Pharmacol. Rev. 20. 1 (1968) and references cited therein. As to racemic PGE₂ see for example W. P. Schneider, Chem. Commun. 304 (1969).

The 16-alkyl and 16-fluoro analogs of PGE₂ and their 15-epimers are represented by the formula:

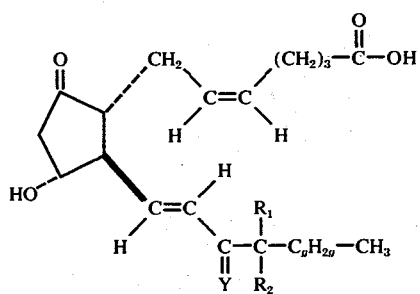

wherein Y is

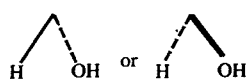

following the usual convention wherein broken line attachment of hydroxy to the side chain at carbon 15 indicates the natural or "α" configuration and solid line attachment of hydroxy indicates the epi or "β" configuration. In certain instances the "S" and "R" nomenclature are used. See Nugteren et al., Nature 212, 38 (1966) and Cahn, J. Chem. Ed. 41, 116 (1964).

In formula II $C_gH_{2g}$ is alkylene of one to 9 carbon atoms, inclusive, with one to 5 carbon atoms, inclusive, in the chain between —CR₁R₂— and terminal methyl; and R₁ and R₂ are hydrogen, methyl, ethyl, or fluoro, being the same or different, with the proviso that at least one of R₁ and R₂ is other than hydrogen, and with the further proviso that R₂ is fluoro only when R₁ is hydrogen or fluoro.

The 16-alkyl and 16-fluoro analogs of PGE₂ and their 15-epimers in their optically active and racemic forms are known. See for example South African Patent No. 72/1936, Derwent Farmdoc No. 71483t; and South African Patent No. 73/2244, Derwent Farmdoc No. 69717U. These analogs are also useful for the above-described pharmacological purposes.

The 16-phenoxy and phenyl-substituted analogs of PGE₂ and their 15-epimers are represented by the formula:

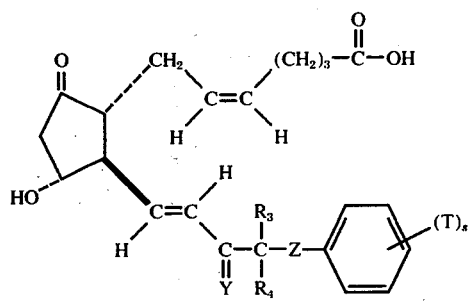

In formula III, R₃ and R₄ are hydrogen, methyl, or ethyl; T is alkyl of one to 4 carbon atoms, inclusive, fluoro, chloro, trifluoromethyl, or —OR₅, wherein R₅ is hydrogen or alkyl of one to 4 carbon atoms, inclusive, and $s$ is zero, one, 2, or 3, with the proviso that not more than two T's are other than alkyl; Y is

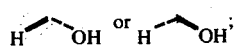

and Z represents an oxa atom (—O—) or $C_jH_{2j}$, wherein $C_jH_{2j}$ is a valance bond or alkylene of one to 9 carbon atoms, inclusive, substituted with zero, one, or 2 fluoro, with one to 6 carbon atoms, inclusive, between —CR₃R₄— and the ring.

The 16-phenoxy and phenyl-substituted analogs of PGE₂ and their 15-epimers in their optically active and racemic forms are known. See for example South African Patent No. 73/2818, Derwent Farmdoc No. 73279U; and British Specification No. 1,324,737, Derwent Farmdoc No. 31279T.

Esters of the above compounds are known, wherein the hydrogen atom of the carboxyl group is replaced by a hydrocarbyl or substituted hydrocarbyl group. Among these are the methyl ester of 16-methyl-PGE₂, the methyl ester of 16,16-dimethyl-PGE₂ (A. Robert et al., Gastroenterology 64, 790 (1973)); the phenyl and alkyl-phenyl esters of 16-fluoro- and 16,16-difluoro-PGE₂ (South African Patent No. 73/2244); the phenyl and alkyl-phenyl esters of 16-phenoxy-PGE₂ (South African Patent No. 73/2818); and the phenyl and alkyl-phenyl esters of phenyl-substituted PGE₂ (British Specification No. 1,324,737).

SUMMARY OF THE INVENTION

It is a purpose of this invention to provide novel ester derivatives of prostaglandin $E_2$ analogs, including certain 16-alkyl, 16-fluoro, 16-phenoxy, and phenyl-substituted analogs, their 15-epimers, and their racemic forms. It is a further purpose to provide such esters derived from substituted phenols and naphthols. It is a further purpose to provide such esters in a free-flowing crystalline form. It is still a further purpose to provide novel processes for preparing these esters.

The presently described esters include compounds represented by the generic formula:

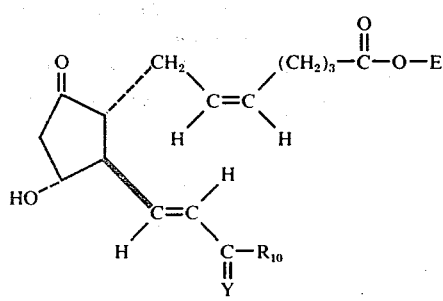     IV wherein Y is

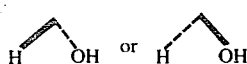

and wherein $R_{10}$ is either

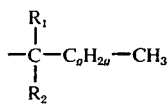     (1)

wherein $C_gH_{2g}$ is alkylene of one to 9 carbon atoms, inclusive, with one to 5 carbon atoms, inclusive in the chain between $-CR_1R_2-$ and terminal methyl; and $R_1$ and $R_2$ are hydrogen, methyl, ethyl, or fluoro, being the same or different, with the proviso that at least one of $R_1$ and $R_2$ is other than hydrogen, and with the further proviso that $R_2$ is fluoro only when $R_1$ is hydrogen or fluoro; or

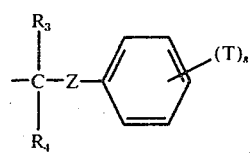     (2)

wherein $R_3$ and $R_4$ are hydrogen, methyl, or ethyl; T is alkyl of one to 4 carbon atoms, inclusive, fluoro, chloro, trifluoromethyl, or $-OR_5$, wherein $R_5$ is hydrogen or alkyl of one to 4 carbon atoms, inclusive, and $s$ is zero, one, 2, or 3, with the proviso that not more than two T's are other than alkyl; Z represents an oxa atom $(-O-)$ or $C_jH_{2j}$, wherein $C_jH_{2j}$ is a valence bond or alkylene of one to 9 carbon atoms, inclusive, substituted with zero, one, or 2 fluoro, with one to 6 carbon atoms, inclusive, between $-CR_3R_4-$ and the ring. In formula IV, E is a substituted phenyl or naphthyl group identified as follows:

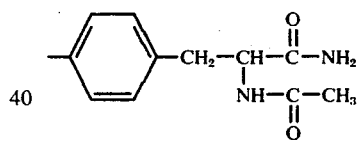     A
B
C
D

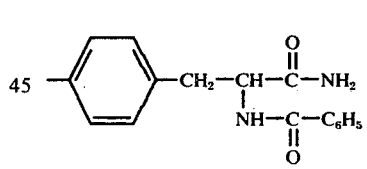     E
F
G

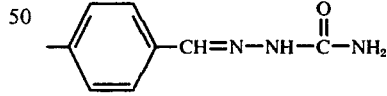     H
I

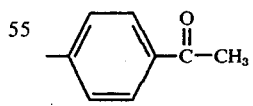     J
K

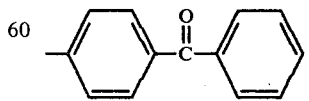     K'
L

-continued

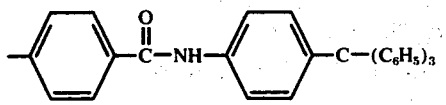  M

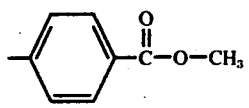  N

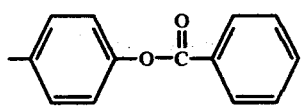  O

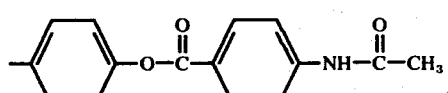  P

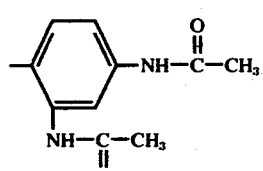  Q

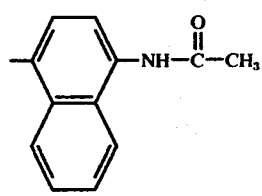  R

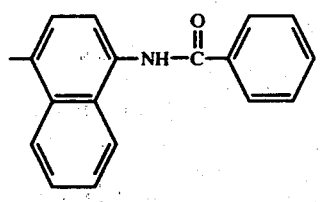  S or

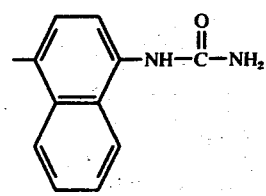  T

For example, the p-acetamidophenyl ester of 16,16-dimethyl-PGE$_2$ is represented by formula IV when R$_{10}$ is

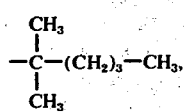

Y is

and E is A, i.e.

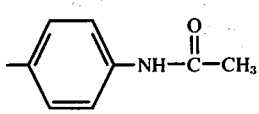

and is conveniently identified herein as the 16,16-dimethyl-PGE$_2$ ester of formula IV-A. Racemic compounds are designated by the prefix "racemic" or "dl"; when that prefix is absent, the intent is to designate an optically active compound.

The novel formula-IV compounds and corresponding racemic compounds of this invention are each useful for the same purposes as described above for PGE$_2$ and are used for those purposes in the same manner known in the art, including oral, sublingual, buccal, rectal, intravaginal, intrauterine, or topical administration.

For many applications these novel prostaglandin esters which I have obtained from certain specified phenols and naphthols have advantages over the corresponding known prostaglandin compounds. Thus, these substituted phenyl and naphthyl esters are surprisingly stable compounds having outstanding shelf-life and thermal stability. In contrast to the acid form of these prostaglandins, these esters are less subject to acid-catalyzed decomposition either by elimination of water or by epimerization. Thus these compounds have improved stability either in solid, liquid, or solution form. In oral administration these esters have shown surprisingly greater efficacy than the corresponding free acids or lower alkyl esters, whether because of longer duration of biological activity or because of improved lipophilicity and absorption is not certain. These esters offer a further advantage in that they have low solubility in water and the body fluids and are therefore retained longer at the site of administration.

A particularly outstanding advantage of many of these substituted phenyl and naphthyl esters is that they are obtained in free-flowing crystalline form, generally of moderately high melting point, in the range 60°-130° C. This form is especially desirable for ease of handling, administering, and purifying. These crystals are highly stable, for example showing practically no decomposition at accelerated storage tests at 65° C., in comparison with liquid alkyl esters or the free acids. This quality is advantageous because the compound does not lose its potency and does not become contaminated with decomposition products.

These crystalline esters also provide a means of purifying these PGE$_2$ analogs, particularly, 16,16-dimethyl-PGE$_2$, 16,16-difluoro-PGE$_2$, 16-phenoxy-17,18,19,20-tetranor-PGE$_2$, and 17-phenyl-18,19,20-trinor-PGE$_2$, which are first converted to one of these esters, recrystallized until pure, and then recovered as the free acid. One method of recovering the free acid is by enzymatic hydrolysis of the ester, for example with a lipase. See German Patent No. 2,242,792, Derwent Farmdoc No. 23047U.

To obtain the optimum combination of stability, duration of biological activity, lipophilicity, solubility, and crystallinity, certain compounds within the scope of formula III are preferred.

One preference is that E is limited to

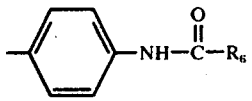

wherein $R_6$ is

—$CH_3$

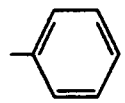

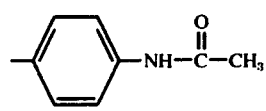

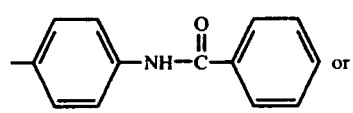 or

—$NH_2$;

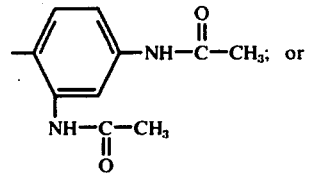

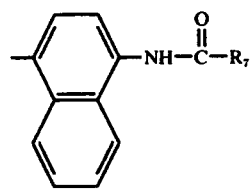

wherein $R_7$ is

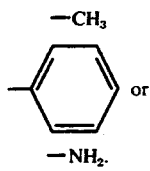

—$NH_2$.

Another preference is that E is limited to

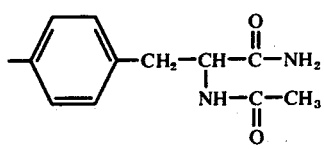

(1)

-continued

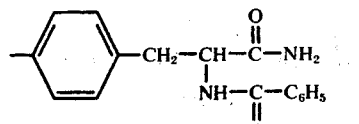

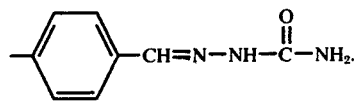

Another preference is that E is limited to

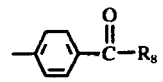  (1)

wherein $R_8$ is

—$CH_3$
—$NH_2$
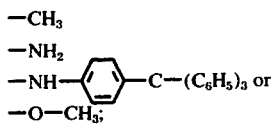
—O—$CH_3$;

or

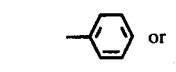  (2)

wherein $R_9$ is (2)

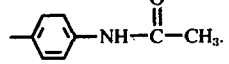 or

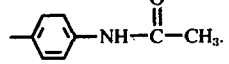—NH—$\overset{O}{\underset{\|}{C}}$—$CH_3$.

(3)

Especially preferred are those compounds which are in free-flowing crystalline form, for example:
p-benzamidophenyl ester of 16,16-dimethyl-PGE$_2$
p-(p-acetamidobenzamido)phenyl ester of 16,16-dimethyl-PGE$_2$
α-semi-carbazono-p-tolyl ester of 16,16-dimethyl-PGE$_2$
p-acetylphenyl ester of 16-phenoxy-17,18,19,20-tetranor-PGE$_2$
p-acetylphenyl ester of 17-phenyl-18,19,20,-trinor-PGE$_2$ The substituted phenyl and naphthyl esters of PGE$_2$ analogs encompassed by formula-IV wherein E is defined by ester groups A through T are produced by the reactions and procedures described and exemplified hereinafter. For convenience, the above prostaglandin or prostaglandin analog is referred to as "the PG compound". The term "phenol" is used in a generic sense, including both phenols and naphthols.

Various methods are available for preparing these esters, differing as to yield and purity of product. Thus, by one method, the PG compound is converted to a tertiary amine salt, reacted with pivaloyl halide to give the mixed acid anhydride and then reacted with the phenol. Alternately, instead of pivaloyl halide, an alkyl or phenylsulfonyl halide is used, such as p-toluenesulfonyl chloride. See for example Belgian Patents Nos. 775,106 and 776,294, Derwent Farmdoc Nos. 33705T and 39011T.

Still another method is by the use of the coupling reagent, dicyclohexylcarbodiimide. See Fieser et al., "Reagents for Organic Synthesis", pp. 231–236, John Wiley and Sons, Inc., New York (1967). The PG compound is contacted with one to ten molar equivalents of the phenol in the presence of 2–10 molar equivalents of dicyclohexylcarbodiimide in pyridine as a solvent.

The preferred novel process for the preparation of these esters, however, comprises the steps (1) forming a mixed anhydride with the PG compound and isobutylchloroformate in the presence of a tertiary amine and (2) reacting the anhydride with an appropriate phenol or naphthol.

The mixed anhydride is represented by the formula:

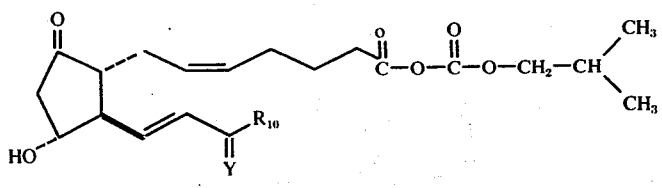

for the optically active PG compounds, $R_{10}$ and Y having the same definition as above.

The anhydride is formed readily at temperatures in the range −40° to +60° C., preferably at −10° to +10° C. so that the rate is reasonably fast and yet side reactions are minimized. The isobutylchloroformate reagent is preferably used in excess, for example 1.2 molar equivalents up to 4.0 per mole of the PG compound. The reaction is preferably done in a solvent and for this purpose acetone is preferred, although other relatively non-polar solvents are used such as acetonitrile, dichloromethane, and chloroform. The reaction is run in the presence of a tertiary amine, for example triethylamine, and the co-formed amine hydrochloride usually crystallizes out, but need not be removed for the next step.

The anhydride is usually not isolated but is reacted directly in solution with the phenol, preferably in the presence of a tertiary amine such as pyridine.

The phenol is preferably used in equivalent amounts or in excess to insure that all of the mixed anhydride is converted to ester. Excess phenol is separated from the product by methods described herein or known in the art, for example by crystallization. The tertiary amine is not only a basic catalyst for the esterification but also a convenient solvent. Other examples of tertiary amines useful for this purpose include N-methylmorpholine, triethylamine, diisopropylethylamine, and dimethylaniline. 2-Methylpyridine and quinoline result in a slow reaction. A highly hindered amine such as 2,6-lutidine is not useful because of the slowness of the reaction.

The reaction with the anhydride proceeds smoothly at room temperature (about 20° to 30° C.) and can be followed in the conventional manner with thin layer chromatography (TLC), usually being found complete within 1–4 hours.

The reaction mixture is worked up to yield the ester following methods known in the art, and the product is purified, for example by silica gel chromatography.

Solid esters are converted to a free-flowing crystalline form on crystallization from a variety of solvents, including ethyl acetate, tetrahydrofuran, methanol, and acetone, by cooling or evaporating a saturated solution of the ester in the solvent or by adding a miscible non-solvent such as diethyl ether, hexane, or water. The crystals are then collected by conventional techniques, e.g. filtration or centrifugation, washed with a small amount of solvent, and dried under reduced pressure. They may also be dried in a current of warm nitrogen or argon, or by warming to about 60° C. Although the crystals are normally pure enough for many applications, they may be recrystallized by the same general techniques to achieve improved purity after each recrystallization.

DESCRIPTION OF THE PREFERRED EMBODIMENTS

The invention can be more fully understood by the following examples.

All temperatures are in degrees centigrade.

Silica gel chromatography, as used herein, is understood to include chromatography on a column packed with silica gel, elution, collection of fractions, and combination of those fractions shown by thin layer chromatography (TLC) to contain the desired product free of starting material and impurities.

"TLC", herein, refers to thin layer chromatography.

PREPARATION 1 p-Benzamidophenol

A solution of p-hydroxyaniline (20 g.) in 200 ml. of pyridine is treated with benzoic anhydride (20 g.). After 4 hr. at about 25° C., the mixture is concentrated under reduced pressure and the residue is taken up in 200 ml. of hot methanol and reprecipitated with 300 ml. of water. The product is recrystallized from hot acetonitrile as white crystals, 8.5 g., m.p. 218.0°–218.5° C.

PREPARATION 2 p-(p-Acetamidobenzamido)phenol

A solution of p-acetamidobenzoic acid (12.5 g.) in 250 ml. of tetrahydrofuran is treated with triethylamine (11.1 ml.). The mixture is then treated with isobutylchloroformate (10.4 ml.) and, after 5 min. at about 25° C., with p-aminophenol (13.3 g.) in 80 ml. of dry pyridine. After 40 min. the crude product is obtained by addition of 2 liters of water. The product is recrystallized from 500 ml. of hot methanol by dilution with 300 ml. of water as white crystals, 5.9 g., m.p. 275.0°–277.0° C.

EXAMPLE 1 p-Benzamidophenyl Ester of 16,16-Dimethyl-PGE$_2$ (Formula IV-B)

A solution of 16,16-dimethyl-PGE$_2$ (Belgian Patent No. 781,978, Derwent Farmdoc No. 75254T) (0.095 g.) and triethylamine (0.055 g.) in 10 ml. of acetone is treated at −10° C. with isobutylchloroformate (0.068 g.) with stirring. After about 10 min. the mixture is treated with p-benzamidophenol (Prep. 1, 0.600 g.) in 6 ml. of pyridine for at least one hour at about 25° C. The solvent is removed under reduced pressure. The crude residue is taken up in 100 ml. of chloroform, washed with 75 ml. of 0.1N aqueous monosodium orthophosphate, dried, and concentrated. The residue is subjected to silica gel chromatography, eluting with ethyl acetate-chloroform (1:1). The title compound obtained by concentration of selected fractions, a gummy solid, 0.05 g., is crystallized from ethyl acetate-hexane as white free-flowing crystals, m.p. 62.3°–64.5° C.

$R_f$ 0.3 (TLC on silica gel plates in ethyl acetateacetic acid (97:3)).

EXAMPLE 2 p-(p-Acetamidobenzamido)phenyl Ester of 16,16-Dimethyl-PGE$_2$ (Formula IV-C)

Following the procedure of Example 1, but using 0.095 g. of 16,16-dimethyl-PGE$_2$, 0.051 g. of triethylamine, 0.068 g. of isobutylchloroformate, and 0.473 g. of p-(p-acetamidobenzamido)phenol (Prep. 2), there is obtained a crude residue. This residue is dissolved in 50 ml. of dimethylformamide and partitioned between 150 ml. of pH 5.5 McIlvaine buffer and 200 ml. of ethyl acetate. The organic layer is dried over sodium sulfate and concentrated. The residue, in 8 ml. of ethyl acetate and 1 ml. of dimethylformamide, is subjected to silica gel chromotography, eluting with ethyl acetate-methanol (97:3) and, subsequently, (92.8). The residue obtained by concentration of selected fractions is the title compound, 0.50 g., and is crystallized from methanol-acetone as white free-flowing crystals, m.p. 126°–128° C., $R_f$ 0.35 (TLC on silica gel plates in ethyl acetate-acetic acid (97:3)).

EXAMPLE 3

α-Semicarbazono-p-tolyl Ester of 16,16-Dimethyl-PGE$_2$ (Formula IV-J)

Following the procedure of Example 1, but using 0.095 g. of 16,16-dimethyl-PGE$_2$, 0.051 g. of triethylamine, 0.068 g. of isobutylchloroformate, and 0.132 g. of p-hydroxybenzaldehyde semicarbazone, there is obtained a crude residue which is taken up in acetonitrile, filtered, and concentrated to a residue. This residue is subjected to silica gel chromatography, eluting with acetonitrile followed by tetrahydrofuran-acetonitrile (3:2). The residue obtained by concentration of selected fractions, 0.06 g., is crystallized from ethyl acetate-hexane a the title compound, white free-flowing crystals, m.p. 84.2°–86.8° C., $R_f$ 0.35 (TLC on silica gel plates in ethyl acetate-acetic acid (97:3)).

EXAMPLE 4 p-Acetylphenyl Ester of 16-Phenoxy-17,18,19,20-tetranor-PGE$_2$ (Formula IV-K)

Following the procedure of Example 1 but using 0.050 g. of 16-phenoxy-17,18,19,20-tetranor-PGE$_2$ (South African Patent No. 73/2818, Derwent Farmdoc. No. 73279U), 0.021 ml. of triethylamine, 0.020 ml. of isobutylchloroformate, and 0.0294 g. of p-hydroxyacetophenone, the reaction mixture is further treated as follows. The mixture is diluted with 20 ml. of ethyl acetate and shaken successively with 0.5 N citric acid and 0.2 N phosphate buffer (pH 7.2). The organic phase is dried over sodium sulfate and concentrated. The residue is subjected to silica gel chromatography, eluting with dichloromethane-acetonitrile-methanol (50:50:1). The residue obtained by concentration of selected fractions is crystallized from ethyl acetate-hexane as the title compound, 0.021 g., m.p. 122.6°–124.2° C., $R_f$ 0.8 (TLC on silica gel in dichloromethane-acetonitrile (3:2)).

EXAMPLE 5 p-Acetylphenyl Ester of 17-Phenyl-18,19,20,-trinor-PGE$_2$ (Formula IV-K)

Following the procedure of Example 1, but using 0.200 g. of 17-phenyl-18,19,20-trinor-PGE$_2$, (Great Britain Specification No. 1,324,737, Derwent Farmdoc No. 31279T), 0.089 ml. of triethylamine, 0.0845 ml. of isobutylchloroformate, and 0.109 g. of p-hydroxyacetophenone, the reaction mixture is further treated as follows. It is diluted to 100 ml. with ethyl acetate and shaken successively with 5% aqueous citric acid and phosphate buffer (pH 7.0). The organic phase is dried over sodium sulfate and concentrated. The oily residue is subjected to silica gel chromatography, eluting with ethyl acetate containing 2.3% water. The residue obtained by concentration of selected fractions is crystallized from ethyl acetate-hexane as the title compound, 0.153 g., m.p. 91.7°–92.7° C., $R_f$ 0.4 (TLC on silica gel in ethyl acetate-water (98:2)).

Following the procedures of Example 1–5 but employing the racemic forms of the PG compounds, there are obtained the corresponding esters of racemic PG compounds.

EXAMPLES 6–80

The substituted phenyl and naphthyl esters of 16,16-dimethyl-PGE$_2$, 16,16-difluoro-PGE$_2$, 16-phenoxy-17,18,19,20-tetranor-PGE$_2$, and 17-phenyl-18,19,20-trinor-PGE$_2$ of Tables 1–IV below are obtained following the procedures of Example 1, wherein the prostaglandin compound is reacted in the presence of triethylamine and isobutylchloroformate with the appropriate hydroxy phenyl or naphthyl compound, listed in the Table. These phenols or naphthols are readily available or prepared by methods described herein or known in the art. The crude products, obtained by concentration under reduced pressure, are purified by means described herein or known in the art, including partitioning, solvent extraction, washing, silica gel chromatography, trituration, or crystallization.

Following the procedures of Examples 6–80 but employing the racemic forms of the PG compounds, there are obtained the corresponding esters of the racemic PG compounds.

TABLE I

Esters of 16,16-Dimethyl-PGE$_2$

| Ex. | Hydroxy Phenyl or Naphthyl Compound | Product 16,16-Dimethyl-PGE$_2$ ester of formula: |
|---|---|---|
| 6 | p-acetamidophenol | IV-A |
| 7 | p-(p-benzamidobenzamido)phenol | IV-D |
| 8 | p-hydroxyphenylurea | IV-E |
| 9 | p-phenylphenol | IV-F |

TABLE I-continued

Esters of 16,16-Dimethyl-PGE$_2$

| Ex. | Hydroxy Phenyl or Naphthyl Compound | Product 16,16-Dimethyl-PGE$_2$ ester of formula: |
|---|---|---|
| 10 | p-tritylphenol | IV-G |
| 11 | N-acetyltyrosinamide | IV-H |
| 12 | N-benzoyltyrosinamide | IV-I |
| 13 | p-hydroxyacetophenone | IV-K |
| 14 | p-hydoxybenzamide | IV-L |
| 15 | N-(p-tritylphenyl)-p-hydroxybenzamide | IV-M |
| 16 | p-hydroxybenzoic acid, methyl ester | IV-N |
| 17 | hydroquinone benzoate | IV-O |
| 18 | hydroquinone, p-acetamidobenzoic acid ester | IV-P |
| 19 | 2,4-diacetamidophenol | IV-Q |
| 20 | 1-acetamido-4-hydroxy-naphthalene | IV-R |
| 21 | 1-benzamido-4-hydroxy-naphthalene | IV-S |
| 22 | 1-hydroxy-4-ureido-naphthalene | IV-T |

TABLE II

Esters of 16,16-Difluoro-PGE$_2$

| Ex. | Hydroxy Phenyl or Naphthyl Compound | Product 16,16-Difluoro-PGE$_2$ ester of formula: |
|---|---|---|
| 23 | p-acetamidophenol | IV-A |
| 24 | p-benzamidophenol | IV-B |
| 25 | p-(p-acetamidobenzamido)phenol | IV-C |
| 26 | p-(p-benzamidobenzamido)phenol | IV-D |
| 27 | p-hydroxyphenylurea | IV-E |
| 28 | p-phenylphenol | IV-F |
| 29 | p-tritylphenol | IV-G |
| 30 | N-acetyltyrosinamide | IV-H |
| 31 | N-benzoyltyrosinamide | IV-I |
| 32 | p-hydroxybenzaldehyde | IV-J |
| 33 | p-hydroxyacetophenone | IV-K |
| 34 | p-hydroxybenzamide | IV-L |
| 35 | N-(p-tritylphenyl)-p-hydroxybenzamide | IV-M |
| 36 | p-hydroxybenzoic acid, methyl ester | IV-N |
| 37 | hydroquinone benzoate | IV-O |
| 38 | hydroquinone, p-acetamidobenzoic acid ester | IV-P |
| 39 | 2,4-diacetamidophenol | IV-Q |
| 40 | 1-acetamido-4-hydroxy-naphthalene | IV-R |
| 41 | 1-benzamido-4-hydroxy-naphthalene | IV-S |
| 42 | 1-hydroxy-4-ureido-naphthalene | IV-T |

TABLE III

Ester of 16-phenoxy-17,18,19,20-tetranor-PGE$_2$

| Ex. | Hydroxy Phenyl or Naphthyl Compound | Product 16-phenoxy-17,18,19,20-tetranor-PGE$_2$ ester of formula: |
|---|---|---|
| 43 | p-acetamidophenol | IV-A |
| 44 | p-benzamidophenol | IV-B |
| 45 | p-(p-acetamidobenzamido)phenol | IV-C |
| 46 | p-(p-benzamidobenzamido)phenol | IV-D |
| 47 | p-hydroxyphenylurea | IV-E |
| 48 | p-phenylphenol | IV-F |
| 49 | p-tritylphenol | IV-G |
| 50 | N-acetyltyrosinamide | IV-H |
| 51 | N-benzoyltyrosinamide | IV-I |
| 52 | p-hydroxybenzaldehyde semicarbazone | IV-J |
| 53 | p-hydroxybenzamide | IV-L |
| 54 | n-(p-tritylphenyl)-p-hydroxybenzamide | IV-M |
| 55 | p-hydroxybenzoic acid, methyl ester | IV-N |
| 56 | hydroquinone benzoate | IV-O |
| 57 | hydroquinone, p-acetamidobenzoic acid ester | IV-P |
| 58 | 2,4-diacetamidophenol | IV-Q |
| 59 | 1-acetamido-4-hydroxy-naphthalene | IV-R |
| 60 | 1-benzamido-4-hydroxynaphthalene | IV-S |
| 61 | 1-hydroxy-4-ureido-naphthalene | IV-T |

TABLE IV

Esters of 17-phenyl-18,19,20-trinor-PGE$_2$

| Ex. | Hydroxy Phenyl or Naphthyl Compound | Product 17-phenyl-18,19,20-trinor-PGE$_2$ ester of formula: |
|---|---|---|
| 62 | p-acetamidophenol | IV-A |
| 63 | p-benzamidophenol | IV-B |
| 64 | p-(p-acetamidobenzamido)phenol | IV-C |
| 65 | p-(p-benzamidobenzamido)phenol | IV-D |
| 66 | p-hydroxyphenylurea | IV-E |
| 67 | p-phenylphenol | IV-F |
| 68 | p-tritylphenol | IV-G |
| 69 | N-acetyltyrosinamide | IV-H |
| 70 | N-benzoyltyrosinamide | IV-I |
| 71 | p-hydroxybenzaldehyde semicarbazone | IV-J |
| 72 | p-hydroxybenzamide | IV-L |
| 73 | N-(p-tritylphenyl)-p-hydroxybenzamide | IV-M |
| 74 | p-hydroxybenzoic acid, methyl ester | IV-N |
| 75 | hydroquinone benzoate | IV-O |
| 76 | hydroquinone, p-acetamidobenzoic acid ester | IV-P |
| 77 | 2,4-diacetamidophenol | IV-Q |
| 78 | 1-acetamido-4-hydroxy-naphthalene | IV-R |
| 79 | 1-benzamido-4-hydroxy-naphthalene | IV-S |
| 80 | 1-hydroxy-4-ureido-naphthalene | IV-T |

I claim:

1. An optically active compound of the formula

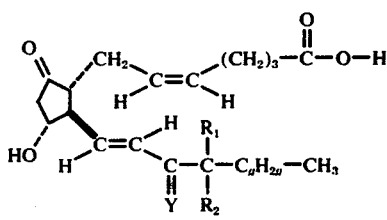

or a racemic mixture of that compound and the enantiomer thereof. Wherein C$_g$H$_{2g}$ is alkylene of one to g carbon atoms inclusive, with one to 5 carbon atoms inclusive, in the chain between —CR$_1$R$_2$— and (terminal methyl: R$_1$ and R$_2$ are hydrogen, methyl, ethyl, or fluoro, being the same or different, with the proviso that at least one of R$_1$ and R$_2$ is other than hydrogen, and with the further proviso that R$_2$ is fluoro only when R$_1$ is hydrogen or fluoro; Y is

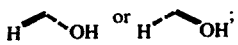

and E is

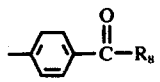  (1)

wherein R$_8$ is

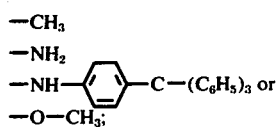

-continued
or

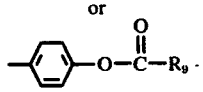  (2)

wherein R$_9$ is

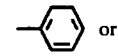 or

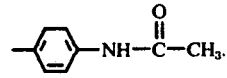

2. The p-hydroxyacetophenone ester of 16,16-dimethyl-PGE$_2$ a compound according to claim 1.

3. The p-hydroxybenzamide ester of 16,16-dimethyl-PGE$_2$, a compound according to claim 1.

4. The N-(p-tritylphenyl)-p-hydroxybenzamide ester of 16,16-dimethyl-PGE$_2$, a compound according to claim 1.

5. The hydroquinone benzoate ester of 16,16-dimethyl-PGE$_2$, a compound according to claim 1.

6. The hydroquinone, p-acetamidobenzoic acid ester of 16,16-dimethyl-PGE$_2$, a compound according to claim 1.

7. The p-hydroxyacetophenone ester of 16,16-difluoro-PGE$_2$, a compound according to claim 1.

8. The p-hydroxybenzamide ester of 16,16-difluoro-PGE$_2$, a compound according to claim 1.

9. The N-(p-tritylphenyl)-p-hydroxybenzamide ester of 16,16-difluoro-PGE$_2$, a compound according to claim 1.

10. The hydroquinone benzoate ester of 16,16-difluoro-PGE$_2$, a compound according to claim 1.

11. The hydroquinone, p-acetamidobenzoic acid ester of 16,16-difluoro-PGE$_2$, a compound according to claim 1.

* * * * *

UNITED STATES PATENT OFFICE
CERTIFICATE OF CORRECTION

Patent No. 4,011,249                    Dated  March 8, 1977

Inventor(s)  Walter Morozowich

It is certified that error appears in the above-identified patent and that said Letters Patent are hereby corrected as shown below:

Column 1, lines 22-24,

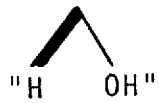

should read

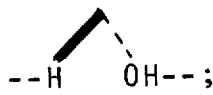

line 27, "PGE$_3$" should read --PGE$_2$--; line 28, "(3s)" should read --(3S)--; lines 28-29, "oxo-isocyclopentyl)" should read --oxo-1α-cyclopentyl}--; line 30, "radical" should read --medical--. Column 2, line 12, "71483t;" should read --71483T;--. Column 8, line 49, "18,19,20,-" should read -- 18,19,20- --. Column 11, line 12, "acetateacetic" should read --acetate-acetic--; line 50, "a" should read --as--. Column 12, line 45, "1-IV" should read --I-IV--. Column 13, Table III, Ex. 54, "n-" should read --N- --.

Column 15, line 38, "g" should read --9--;
line 39, "atoms" should read --atoms,--; line 40, "(termi-" should read --termi- --; line 41, "methyl:" should read --methyl;--.

Signed and Sealed this thirtieth Day of August 1977

[SEAL]

Attest:

RUTH C. MASON
Attesting Officer

C. MARSHALL DANN
Commissioner of Patents and Trademarks